US007662088B2

(12) United States Patent
McCaffrey

(10) Patent No.: US 7,662,088 B2
(45) Date of Patent: Feb. 16, 2010

(54) ADULT SEXUAL NOVELTY DEVICE FOR THOSE PHYSICALLY CHALLENGED

(76) Inventor: Thomas J. McCaffrey, 548 Padilla St., San Gabriel, CA (US) 91776

(*) Notice: Subject to any disclaimer, the term of this patent is extended or adjusted under 35 U.S.C. 154(b) by 706 days.

(21) Appl. No.: 11/508,485

(22) Filed: Aug. 23, 2006

(65) Prior Publication Data

US 2008/0081946 A1 Apr. 3, 2008

(51) Int. Cl.
*A61F 5/00* (2006.01)

(52) U.S. Cl. .......................................................... 600/38

(58) Field of Classification Search ............. 600/38-41; 601/46, 79, 80, 81; 403/8, 252-255, 264

See application file for complete search history.

(56) References Cited

U.S. PATENT DOCUMENTS 4,124,317 A * 11/1978 Dauth .......................... 403/8
5,690,603 A 11/1997 Kain
5,848,980 A * 12/1998 Demerais .................... 601/46
6,179,795 B1 1/2001 Garza
6,540,667 B2 4/2003 Hickman
6,656,139 B2 12/2003 Zwezdaryk
6,991,599 B2 * 1/2006 Hudson ....................... 600/38
2005/0033112 A1 2/2005 Burton et al.

* cited by examiner

*Primary Examiner*—Samuel G Gilbert
(74) *Attorney, Agent, or Firm*—Richard L. Miller

(57) ABSTRACT

An adult sexual novelty device for those physically challenged which comprises a handle. A first stimulating component is provided. A mechanism is for attaching the first stimulating component at a right angle and in an adjustable manner near to a first end of the handle for insertion into an orifice of a person. A second stimulating component is also provided. Another mechanism is for attaching the second stimulating component at a right angle and in an adjustable manner near to a second end of said handle for insertion into an orifice of a person. The first stimulating component and the second stimulating component are in a parallel relationship to each other, to be used as prescribed by a physician, therapist and persons having special expert professional knowledge in the field.

10 Claims, 2 Drawing Sheets

ADULT SEXUAL NOVELTY DEVICE FOR THOSE PHYSICALLY CHALLENGED

BACKGROUND OF THE INVENTION

1. Field of the Invention

The present invention relates to a stimulating apparatus, and more particularly, an adult sexual novelty device for those physically challenged.

2. Description of the Prior Art

Numerous innovations for sexual aid devices have been provided in the prior art that will be described. Even though these innovations may be suitable for the specific individual purposes to which they address, however, they differ from the present invention.

A FIRST EXAMPLE, Office Document U.S. Pat. No. 6,179,795 B1, Issued on Jan. 30, 2001, to Garza teaches an adult novelty device for simulating sexual encounters by a user lying in a reclined position. The device includes a pivot base aligned along an axis perpendicular to the length of the user and generally within the plane of the reclined position. A leg portion, joined to the pivot base by a knee joint, extends upward to permit the leg portion to move in an arc closer to and away from the user. A sleeve assembly is mounted on the leg portion and is aligned for sexual engagement with the user in at least one body orifice by a sleeve mounted on the other end of the assembly. The user is able to move the sleeve by a driver assembly attached to the leg, whereby the user can move the leg portion toward and away from the user's body orifice by pivoting the leg portion about the knee joint to cause movement of the sleeve assembly. In a preferred embodiment, the pivot base includes a pair of pivot base blocks holding down a base rod on both ends of the base rod, whereby the knee joint pivots on the rod to permit rotation of the knee joint about the rod. Also preferred is to adjustably mount the sleeve assembly and/or the driver assembly on the leg to permit adjustment of the angle with respect to the horizontal position of the user.

A SECOND EXAMPLE, Office Document U.S. Pat. No. 6,540,667 B2, Issued on Apr. 1, 2003, to Hickman teaches a sexual assistance device and methods which may be used as a marital aid which include two elongate members secured by a pivotal connection. A biasing element, such as a spring coil, is disposed at or adjacent the pivotal connection for biasing the opposite ends of the two elongate members away from each other. Respective supports are provided at the two opposite ends of the two elongate members which are engageable with the operator's legs. A sexually stimulating element, such as a vibrator or the like, is preferably removably attached to the pivotal connection. Thus, the operator may produce reciprocal longitudinal movement inwardly and outwardly, relative to the operator's body, by compressing and uncompressing the two elongate members with the legs of the operator thereby fully controlling movement of the sexually stimulating element by the legs of the operator. The biasing force is preferably relatively weak so as to permit easy closing of the operator's legs while still providing a suitable force to permit the legs to securely contact the ends of the two elongate members.

A THIRD EXAMPLE, Office Document U.S. Pat. No. 6,656,139 B2, Issued on Dec. 2, 2003, to Zwezdaryk teaches a vibrator that has a base member and elongated flexible elements extending from the base member for contacting a user. A vibrator includes vibration means that is mounted within the vibrator of causing the vibrator to vibrate. The elongated flexible elements are positionable by a user in a plurality of configurations, as desired.

A FOURTH EXAMPLE, U.S. Patent Office Document No. 2005/0033112 A1, Published on Feb. 10, 2005, to Bruton et al. teaches a sexual aid device that includes a housing having a generally cylindrical base and central portion and an upper portion defining a closed upper end. The base includes an open lower end and at least the base and central portion are hollow. The housing is fabricated of a lubricious glass-based single piece of material. An electric motor is mounted in the hollow central portion of the housing and vibrator means including a block and an eccentric drive therefore is coupled to the motor. A battery means is disposed in the hollow base of the housing and is operably coupled with the motor. The motor and battery means are connected in series circuit and an end sealing means including a cap mounted on the open end of the base for releasably sealing the open end so that the hollow interior of the housing is waterproof when the cap is mounted on the base. The end sealing means provides an external switch means operably coupled with the battery means and the motor for selectively energizing the motor to drive the block in eccentric rotation to thereby cause the housing to vibrate.

It is apparent now that numerous innovations for sexual aid devices have been provided in the prior art that are adequate for various purposes. Furthermore, even though these innovations may be suitable for the specific individual purposes to which they address, accordingly, they would not be suitable for the purposes of the present invention as heretofore described.

SUMMARY OF THE INVENTION

AN OBJECT of the present invention is to provide an adult sexual novelty device for those physically challenged that avoids, the disadvantages of the prior art.

ANOTHER OBJECT of the present invention is to provide an adult sexual novelty device for those physically challenged that is simple and inexpensive to manufacture.

STILL ANOTHER OBJECT of the present invention is to provide an adult sexual novelty device for those physically challenged that is simple to use.

BRIEFLY STATED, STILL YET ANOTHER OBJECT of the present invention is to provide an adult sexual novelty device for those physically challenged that comprises a handle. A first stimulating component is provided. A mechanism is for attaching the first stimulating component at a right angle and in an adjustable manner near to a first end of the handle for insertion into an orifice of a person. A second stimulating component is also provided. Another mechanism is for attaching the second stimulating component at a right angle and in, an adjustable manner near to a second end of the handle for insertion into an orifice of a person. The first stimulating component and the second stimulating component are in a parallel relationship to each other, to be used as prescribed by a physician, therapist and persons having special expert professional knowledge in the field.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawings are briefly described as follows.

A MARSHALLING OF REFERENCE NUMERALS UTILIZED IN THE DRAWING

Figure 1:
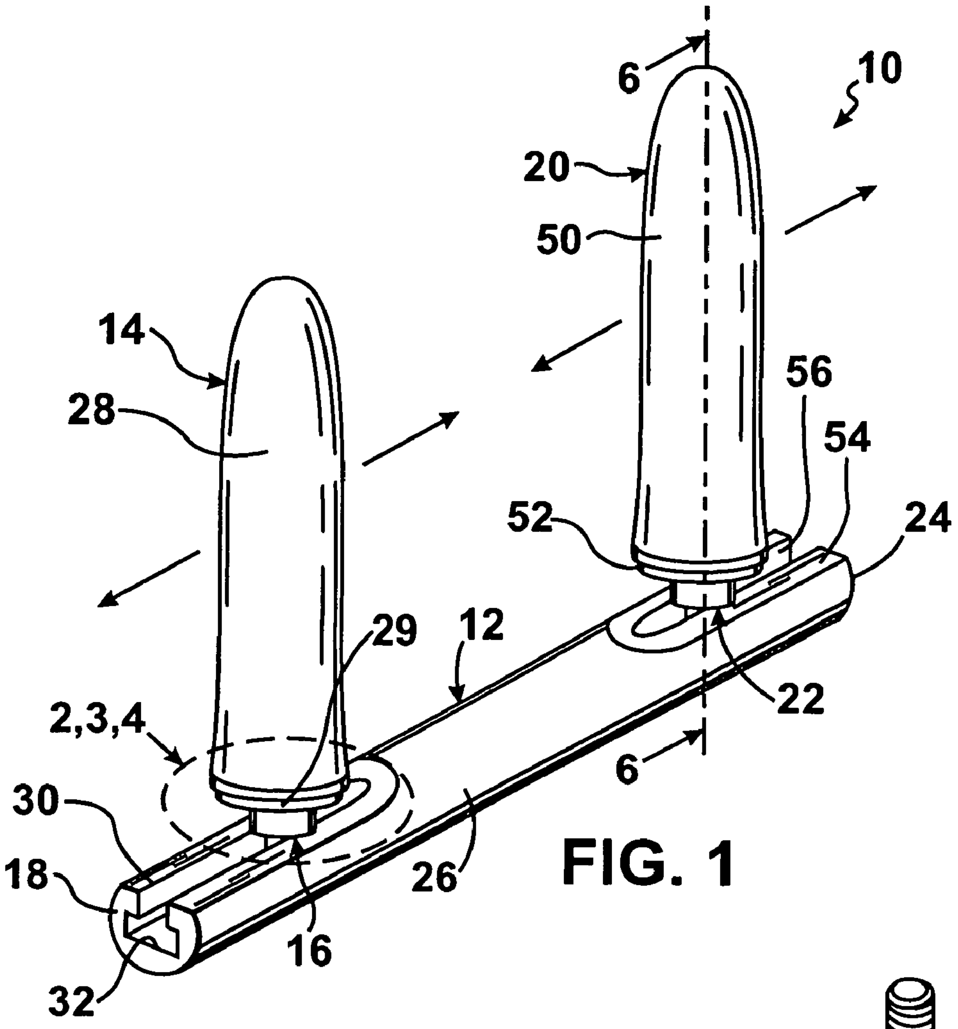
FIG. 1 is a diagrammatic perspective view of the present invention.

10 adult sexual novelty device
12 handle of device 10
14 first stimulating component of device 10
16 first attaching mechanism of device 10
18 first end of handle 12
20 second stimulating component of device 10
22 second attaching mechanism of device 10
24 second end of handle 12
26 rigid cylindrical rod shaped member for handle 12
28 first cone shaped sleeve 28 for first stimulating component 14
29 first flat base of first cone shaped sleeve 28
30 first flat top portion of handle 12
32 inverted first T-shaped slot in handle 12
34 first T-shaped bolt of first attaching mechanism 16
36 first T-shaped head of first T-shaped bolt 34
38 first threaded shaft of first T-shaped bolt 34
40 first compression bushing of first attaching mechanism 16
42 first central aperture in first compression bushing 40
44 first flat washer of first attaching mechanism 16
46 first central hole in first flat washer 44
48 first central bore in first flat base 29
50 second cone shaped sleeve for second stimulating component 20
52 second flat base of second cone shaped sleeve 50
54 second flat top portion of handle 12
56 inverted second T-shaped slot handle 12
58 second T-shaped bolt of second attaching mechanism 22
60 second T-shaped head of second T-shaped bolt 58
62 second threaded shaft of second T-shaped bolt 58
64 second compression bushing of second attaching mechanism 22
68 second central aperture in second compression bushing 64
70 second flat washer of second attaching mechanism 22
72 second central hole in second flat washer 70
74 second central threaded bore in second flat base 52
76 electromechanical apparatus in second stimulating component 20

DETAILED DESCRIPTION OF THE PREFERRED EMBODIMENT

Referring now to the figures, in which like numerals indicate like parts, and particularly to FIG. 1, which is a diagrammatic perspective view of the present invention, and as such, will be discussed with reference thereto.

The present invention is an adult sexual novelty device 10 for those physically challenged which comprises a handle 12. A first stimulating component 14 is provided. A mechanism 16 is for attaching the first stimulating component 14 at a right angle and in an adjustable manner near to a first end 18 of the handle 12 for insertion into an orifice of a person. A second stimulating component 20 is also provided. Another mechanism 22 for attaching the second stimulating component 20 at a right angle and in an adjustable manner near to a second end 24 of the handle 12 for insertion into an orifice of a person. The first stimulating component 14 and the second stimulating component 20 are in a parallel relationship to each other, to be used as prescribed by a physician, therapist and persons having special expert professional knowledge in the field.

Figure 2:
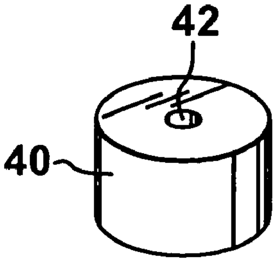
FIGS. 2, 3, 4 are diagrammatic perspective views of the assembly components enclosed in the dotted curve indicated by arrow 2,3,4 in FIG. 1.
Figure 3:
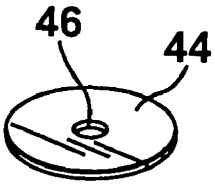
Figure 4:
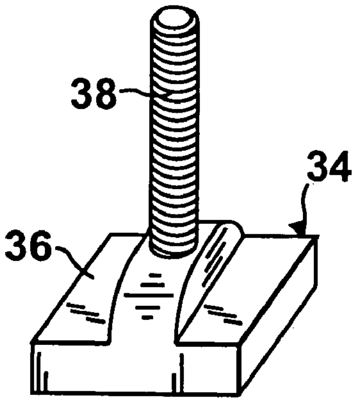
Figure 5:
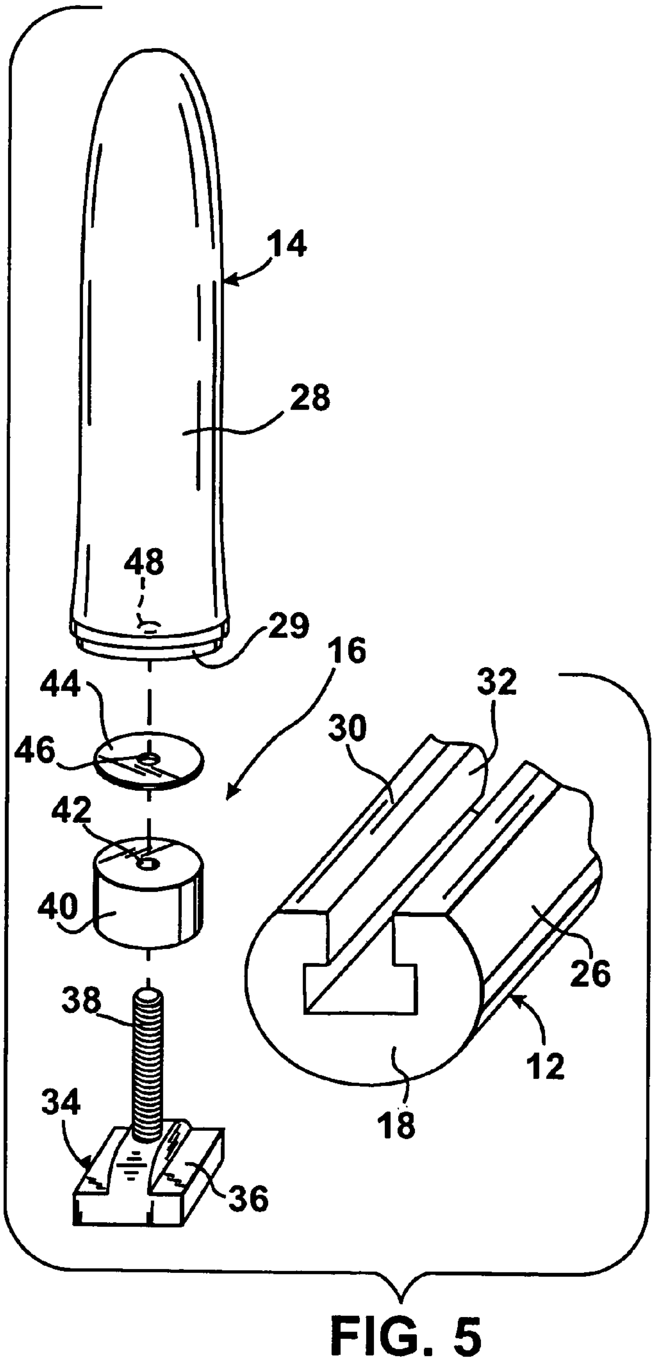
FIG. 5 is a diagrammatic perspective view, with parts broken away, showing a set of components of the present invention exploded before assembly.

FIGS. 2, 3, 4 are diagrammatic perspective views of the assembly components enclosed in the dotted curve indicated by arrow 2,3,4 in FIG. 1, while FIG. 5 is a diagrammatic perspective view, with parts broken away, showing a set of components of the present invention exploded before assembly, and as such, will be discussed with reference thereto.

The handle 12 of the device 10 comprises a rigid cylindrical rod shaped member 26. The first stimulating component 14 of the device 10 comprises a first cone shaped sleeve 28 that has a first flat base 29. The first attaching mechanism 16 comprises the handle 12 having a first flat top portion 30 extending horizontally from the first end 18 and an inverted first T-shaped slot 32 extending upwardly through the first flat top portion. A first T-shaped bolt 34 has a first T-shaped head 36 and a first threaded shaft 38. The first T-shaped head 36 slides within the inverted first T-shaped slot 32 in the handle 12 with the first threaded shaft 38 extending outwardly from the first flat top portion 30 of the handle 12.

A first compression bushing 40 has a first central aperture 42 therethrough. The first central aperture 42 of the first compression bushing 40 fits over the first threaded shaft 38 of the first T-shaped bolt 34 and onto the first flat top portion 30 of the handle 12. A first flat washer 44 has a first central hole 46 therethrough. The first central hole 46 of the first flat washer 44 fits over the first threaded shaft 38 of the first T-shaped bolt 34 and onto the first compression bushing 40. The first flat base 29 of the first cone shaped sleeve 28 of the first stimulating component 14 has a first central threaded bore 48 therethrough. When the first central threaded bore 48 of the first flat base 29 is manually threaded onto the first threaded shaft 38, the first flat base 29 will be tightly pressed against the first flat washer 44.

Figure 6:
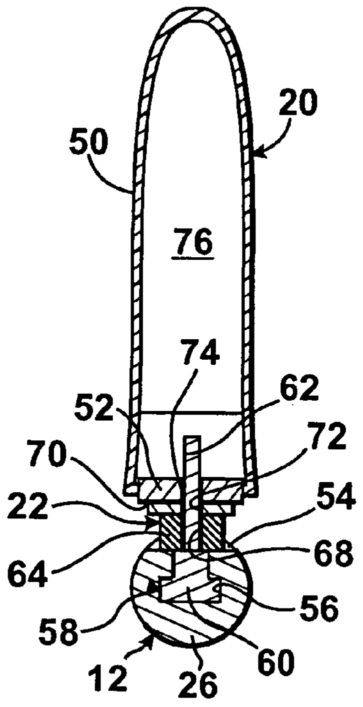
FIG. 6 is a diagrammatic cross sectional view taken on line 6-6 of FIG. 1.

FIG. 6 is a diagrammatic cross sectional view taken on line 6-6 of FIG. 1, and as such, will be discussed with reference thereto. The second stimulating component 22 of the device 10 comprises a second cone shaped sleeve 50 that has a second flat base 52.

The second attaching mechanism 22 comprises the handle 12 having a second flat top portion 54 extending horizontally from the second end 24 and an inverted second T-shaped slot 56 extending upwardly through the second flat top portion 54 (see FIG. 1). A second T-shaped bolt 58 has a second T-shaped head 60 and a second threaded shaft 62. The second T-shaped head 60 slides within the inverted second T-shaped slot 56 in the handle 12 with the second threaded shaft 62 extending outwardly from the second flat top portion 54 of the handle 12. A second compression bushing 64 has a second central aperture 68 therethrough. The second central aperture 68 of the second compression bushing 64 fits over the second threaded shaft 62 of the second T-shaped bolt 58 and onto the second flat top portion 54 of the handle 12.

A second flat washer 70 has a second central hole 72 therethrough. The second central hole 72 of the second flat washer 70 fits over the second threaded shaft 62 of the second T-shaped bolt 58 and onto the second compression busing 64. The second flat base 52 of the second cone shaped sleeve 50 of the second stimulating component 20 has a second central threaded bore 74 therethrough. When the second central threaded bore 74 of the second flat base 52 is manually threaded onto the second threaded shaft 62, the second flat base 52 will be tightly pressed against the second flat washer 70.

The second stimulating component 20 can further comprise an electromechanical apparatus 76 therein to be utilized by the physically challenged. The electromechanical apparatus 76 can be a vibrator, a heater, or a medication dispenser.

It will be understood that each of the elements described above, or two or more together, may also find a useful application in other types of constructions differing from the types described above.

While the invention has been illustrated and described as embodiments of an adult sexual novelty device for those physically challenged, accordingly it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An adult sexual novelty device for those physically challenged which comprises:

a) a handle;

b) a first stimulating component;

c) means for attaching said first stimulating component at a right angle and in an adjustable manner near to a first end of said handle for insertion into an orifice of a person;

d) a second stimulating component; and e) means for attaching said second stimulating component at a right angle and in an adjustable manner near to a second end of said handle for insertion into an orifice of a person, wherein said first stimulating component and said second stimulating component are in a parallel relationship to each other, to be used as prescribed by a physician, therapist and persons having special expert professional knowledge in the field.

2. The device as recited in claim 1, wherein said handle comprises a rigid cylindrical rod shaped member.

3. The device as recited in claim 1, wherein said first stimulating component comprises a first cone shaped sleeve having a first flat base.

4. The device as recited in claim 3, wherein said first attaching means comprises:

a) said handle having a first flat top portion extending horizontally from said first end and an inverted first T-shaped slot extending upwardly through said first flat top portion;

b) a first T-shaped bolt having a first T-shaped head and a first threaded shaft, wherein said first T-shaped head slides within said inverted first T-shaped slot in said handle with said first threaded shaft extending outwardly from said first flat top portion of said handle;

c) a first compression bushing having a first central aperture therethrough, wherein said first central aperture of said first compression bushing fits over said first threaded shaft of said first T-shaped bolt and onto said first flat top portion of said handle;

d) a first flat washer having a first central hole therethrough, wherein said first central hole of said first flat washer fits over said first threaded shaft of said first T-shaped bolt and onto said first compression bushing; and e) said first flat base of said first cone shaped sleeve of said first stimulating component having a first central threaded bore therethrough, wherein when said first central threaded bore of said first flat base is manually threaded onto said first threaded shaft, said first flat base will be tightly pressed against said first flat washer.

5. The device as recited in claim 1, wherein said second stimulating component comprises a second cone shaped sleeve having a second flat base.

6. The device as recited in claim 5, wherein said second attaching means comprises:

a) said handle having a second flat top portion extending horizontally from said second end and an inverted second T-shaped slot extending upwardly through said second flat top portion;

b) a second T-shaped bolt having a second T-shaped head and a second threaded shaft, wherein said second T-shaped head slides within said inverted second T-shaped slot in said handle with said second threaded shaft extending outwardly from said second flat top portion of said handle;

c) a second compression bushing having a second central aperture therethrough, wherein said second central aperture of said second compression bushing fits over said second threaded shaft of said second T-shaped bolt and onto said second flat top portion of said handle;

d) a second flat washer having a second central hole therethrough, wherein said second central hole of said second flat washer fits over said second threaded shaft of said second T-shaped bolt and onto said second compression bushing; and e) said second flat base of said second cone shaped sleeve of said second stimulating component having a second central threaded bore therethrough, wherein when said second central threaded bore of said second flat base is manually threaded onto said second threaded shaft, said second flat base will be tightly pressed against said second flat washer.

7. The device as recited in claim 1, wherein said second stimulating component_ further comprises an electromechanical apparatus therein to be utilized by the physically challenged.

8. The device as recited in claim 7, wherein said electromechanical apparatus comprises a vibrator.

9. The device as recited in claim 7, wherein said electromechanical apparatus comprises a heater.

10. The device as recited in claim 7, wherein said electromechanical apparatus comprises a medication dispenser.

* * * * *